US007211381B1

(12) United States Patent
Yu et al.

(10) Patent No.: US 7,211,381 B1
(45) Date of Patent: *May 1, 2007

(54) β2 ANDRENERGIC POLYMORPHISM DETECTION

(75) Inventors: Hong Yu, Long Grove, IL (US); Barbara T. Merchant, Wilmette, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,718

(22) Filed: Apr. 4, 2000

(51) Int. Cl.
*C12Q 1/68* (2006.01)
*C12P 19/34* (2006.01)
*C07H 21/04* (2006.01)

(52) U.S. Cl. .................. 435/6; 435/91.2; 435/810; 536/23.5; 536/24.31; 536/24.33

(58) Field of Classification Search ............ 435/6, 435/15, 91.2, 194; 536/23.1, 23.5, 24.31, 536/24.33
See application file for complete search history.

(56) References Cited

U.S. PATENT DOCUMENTS

| 4,948,882 | A | | 8/1990 | Ruth .......................... 536/27 |
| 5,142,047 | A | | 8/1992 | Summerton et al. ......... 544/118 |
| 5,185,444 | A | | 2/1993 | Summerton et al. .......... 544/81 |
| 5,210,015 | A | | 5/1993 | Gelfand et al. ................ 435/6 |
| 5,310,652 | A | | 5/1994 | Gelfand et al. ................ 435/6 |
| 5,322,770 | A | | 6/1994 | Gelfand .......................... 435/6 |
| 5,424,414 | A | | 6/1995 | Mattingly ................. 536/25.32 |
| 5,464,746 | A | | 11/1995 | Fino .............................. 435/6 |
| 5,679,635 | A | * | 10/1997 | Matalon et al. ................ 435/6 |
| 5,925,517 | A | | 7/1999 | Tyagi et al. ................... 435/6 |
| 6,593,092 | B2 | * | 7/2003 | Yu et al. ........................ 435/6 |

FOREIGN PATENT DOCUMENTS

| WO | 9220702 | 11/1992 |
| WO | 98/39477 | * 9/1998 |

OTHER PUBLICATIONS

Dewar, J.C. et al. J. Allerg. Clin. Immunol. 100(2):261-265, Aug. 1997.*
Drazen, J.M., et al., THORZX, 1996, 51:1168.
Liggett, S.B., Am. J. Respir. Crit. Care Med., 1997, 156:S156-62.
Martinez, F.D., et al., J. Clin. Invest., 1997, 100:3184-8.
Aynacioglu A S et al: Population frequency, mutation linkage and analytical methodology for the Arg16Gly, Gln27Glu and Thr164Ile polymorphisms in the beta2-adrenergic receptor among Turks. British Journal of Clinical Pharmacology, vol. 48, No. 5, Nov. 1999, pp. 761-764, XP002215090 ISSN: 0306-5251.
Lima John J et al: "Impact of genetic polymorphisms of the beta2-adrenergic receptor on albuterol bronchodilator pharmacodynamics." Clincial Pharmacology & Therapeutics, vol. 65, No. 5, May 1999, pp. 519-525, XP008008579 ISSN: 0009-9236.

* cited by examiner

*Primary Examiner*—Diana B. Johannsen

(57) ABSTRACT

Nucleic acid sequences are provided that are useful as amplification primers and hybridization probes for amplifying and detecting target sequence from the β2 adrenergic receptor gene. The primers and probes can be employed in amplification based methods for detecting the presence of the target sequence in a test sample.

10 Claims, No Drawings

SEQUENCE LISTING

<160> NUMBER OF SEQ ID NOS: 5

<210> SEQ ID NO 1
<211> LENGTH: 106
<212> TYPE: DNA
<213> ORGANISM: Artificial Sequence
<220> FEATURE:
<223> OTHER INFORMATION: Primer

<400> SEQUENCE: 1
aacggcagcg ccttcttgct ggcacccaat agaagccatg cgccggacca cgacgtcacg    60
cagcaaaggg acgaggtgtg ggtggtgggc atgggcatcg tcatgt    106

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
aacggcagcg ccttcttgc    19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
acatgacgat gcccatgcc    19

<210> SEQ ID NO 4
<211> LENGTH: 15
<212> TYPE: DNA
<213> ORGANISM: Artificial Sequence
<220> FEATURE:
<223> OTHER INFORMATION: Probe

<400> SEQUENCE: 4
caatagaagc catgc    15

```
<210> SEQ ID NO 5
<211> LENGTH: 13
<212> TYPE: DNA
<213> ORGANISM: Artificial Sequence
<220> FEATURE:
<223> OTHER INFORMATION: Probe

<400> SEQUENCE: 5
cccaatggaa gcc                                                        13
```

β2 ANDRENERGIC POLYMORPHISM DETECTION

TECHNICAL FIELD

The present invention relates to nucleic acid polymorphisms and, in particular, relates to detecting a single nucleotide polymorphism using nucleic acid amplification technology.

BACKGROUND OF THE INVENTION

Studies designed to determine the sequence of the human genome, as well as studies designed to compare human genomic sequences, have elicited information regarding polymorphisms in the human genome. A wide variety of polymorphisms in the human genome have previously been described. The various types of human genetic polymorphisms include single base substitutions; insertions or deletions; variable numbers of tandem repeats; deletions of all or a large part of a gene; gene amplifications; and chromosomal rearrangements. Generally, polymorphisms that involve a single nucleotide are called single nucleotide polymorphisms ("SNPs").

Recently, a SNP in codon 16 of the β2 adrenergic receptor gene has been reported and associated with a variation in response to β agonist therapy (Drazen, J M et al, Thorzx, 1996, 51:1168; Liggett, S. B., Am. J. Respir. Crit. Care Med., 1997, 156:S156–62; Martinez, F. D. et al, J. Clin. Invest., 1997, 100:3184–8). Adrenergic receptors are hormone receptors on the surfaces of various cells. When bound to an adrenergic receptor site, a hormone can trigger a cascade of cellular events. Hence, adrenergic receptors and the hormones that bind to them, in large part form the mechanism that controls cellular events at a molecular level. Many pharmacological compounds mimic molecules that bind to adrenergic receptor sites and, in this manner, clinically regulate cellular function. For example, a class of drugs known as beta-agonists bind to β2 adrenergic receptor sites and are widely used as a medication for aesthma. Individuals with a SNP in codon 16 of the β2 adrenergic gene, however, may not respond to such therapies do to a conformational, or other, change in the receptor that causes a decrease in the affinity between the receptor and the medication or hormone.

It would therefore be advantageous to provide a means for detecting the polymorphism in codon 16 of the β2 adrenergic receptor gene prior to prescribing medications that would not be efficacious as a result of the polymorphism.

BRIEF DESCRIPTION OF THE INVENTION

Provided herein are methods capable of analyzing polymorphic nucleic acid sequences in a manner suitable for automation. The present invention provides reagents, methods, and kits for amplifying and detecting a target sequence having a polymorphism at codon 16 of the β2 adrenergic receptor gene in a test sample. In particular, SEQ. ID. Nos. 2 and 3 can be employed as amplification primers to amplify the target sequence designated herein as SEQ. ID. NO.1. It was discovered that these primers specifically and sensitively produce an amplification product that is amenable to detection with SEQ. ID. NO. 4 and SEQ. ID. NO. 5. SEQ. ID. NO. 4 is an internal hybridization probe specific for the wild-type sequence and SEQ. ID. NO. 5 is an internal hybridization probe specific for the polymorphic sequence.

The target sequence, designated herein as SEQ. ID. NO. 1, can be amplified by forming a reaction mixture comprising nucleic acid amplification reagents, a test sample containing a target sequence, and a primers designated SEQ ID NOs. 2 and 3. Following amplification, the amplified target sequence can be detected. For example, the probes designated SEQ ID NOs. 4 and 5 can be employed to hybridize to the amplified target sequence to form a probe/amplification product hybrid which then can be detected using any of a variety of well known techniques. Hence, detecting a probe/amplification product hybrid wherein the probe is SEQ. ID. NO. 4 indicates the presence of the wild-type sequence. On the other hand, detecting of a probe/amplification product hybrid wherein the probe is SEQ. ID. NO. 5 would indicate the presence of the polymorphic sequence.

DETAILED DESCRIPTION OF THE INVENTION

As previously mentioned, the present invention provides reagents, methods, and kits for amplifying and detecting a target sequence in a test sample. In particular, SEQ. ID. Nos. 2 and 3 can be employed as amplification primers to amplify a nucleic acid sequence potentially comprising the polymorphism in codon 16 of the β2 adrenergic receptor gene. Hence, both the wild-type and polymorphic version of the target sequence can be amplified using SEQ. ID. NOs. 2 and 3. SEQ. ID. NO. 1 is presented as a representative target sequence. Probe sequences, having SEQ. ID. Nos. 4 and 5 can be employed to detect or distinguish the amplification product produced by primers designated SEQ. ID. NOs. 2 and 3 (e.g. indicate the presence of the wild-type or polymorphic sequence in the test sample).

The primer and probe sequences disclosed herein, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference. It will be understood, however, that sequences employed as primers should at least comprise DNA at the 3' end of the sequence and preferably are completely comprised of DNA.

A "target sequence" as used herein means a nucleic acid sequence that is detected, amplified, both amplified and detected, or otherwise is complementary to one of the sequences herein provided. While the term target sequence is sometimes referred to as single stranded, those skilled in the art will recognize that the target sequence may actually be double stranded.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like. Most typically, the test sample will be whole blood.

SEQ. ID. NOs. 2 and 3 can be used as amplification primers according to amplification procedures well known in the art to amplify the target sequence. Preferably, the sequences provided herein are employed according to the principles of the polymerase chain reaction (PCR) described in U.S. Pat. Nos. 4,683,195 and 4,683,202 which are herein incorporated by reference. It will be understood by those skilled in the art that in the event that the target sequence is RNA, a reverse transcription step can be included in the amplification of the target sequence. Enzymes having reverse transcriptase activity are well known for their ability to produce a DNA sequence from an RNA template. Reverse transcription PCR (RT PCR) is well known in the art and described in U.S. Pat. Nos. 5,310,652 and 5,322,770 which are herein incorporated by reference.

Thus, amplification methods of the present invention generally comprise the steps of forming a reaction mixture comprising nucleic acid amplification reagents, amplification primers (i.e. SEQ. ID. NO. 2 or 3), and a test sample suspected of containing a target sequence. Upon formation of the reaction mixture, the so-formed reaction mixture is subjected to amplification conditions to generate at least one copy of the target sequence. It will be understood that subjecting the reaction mixture may be repeated several times such as by thermal cycling the reaction mixture as is well known in the art:

As stated above, the reaction mixture comprises "nucleic acid amplification reagents" that include reagents which are well known and may include, but are not limited to, an enzyme having polymerase activity (and, as necessary, reverse transcriptase activity), enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

"Amplification conditions" are defined generally as conditions which promote hybridizing or annealing of primer sequences to a target sequence and subsequent extension of the primer sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

Amplification products produced as above can be detected during or subsequently to the amplification of the target sequence. Detection platforms that can be employed to detect the amplification products produced with SEQ. ID. NOs. 2 and 3 using probe sequences having SEQ. ID. NOs. 4 and 5 include any of the well known homogeneous or heterogeneous techniques well known in the art. Examples of homogeneous detection platforms include the use of FRET labels attached to probes that emit a signal in the presence of the target sequence. So-called TaqMan assays described in U.S. Pat. No. 5,210,015 (herein incorporated by reference) and Molecular Beacon assays described in U.S. Pat. No. 5,925,517 (herein incorporated by reference) are examples of techniques that can be employed to homogeneously detect nucleic acid sequences. Additionally, such platforms can be employed to detect the production of amplification product in a real-time manner. It will be understood that the probes can be modified to such that they are suitable for use according to the particular detection platform employed.

Gel electrophoresis, for example, can be employed to detect the products of an amplification reaction after its completion using molecular weight markers. However, amplification products can be detected heterogeneously using labeled probes and solid supports. Hence, methods for detecting the amplified target sequence include the steps of (a) hybridizing at least one hybridization probe (i.e. SEQ. ID. NOs. 4 and 5) to the nucleic acid sequence complementary to the target sequence, so as to form a hybrid comprising the probe and the nucleic acid sequence complementary to the probe; and (b) detecting the hybrid as an indication of the presence of the presence of the target sequence in the test sample.

Hybrids formed as above can be detected using microparticles and labels that can be used to separate and detect such hybrids. Preferably, detection is performed according to the protocols used by the commercially available Abbott LCx® instrumentation (Abbott Laboratories; Abbott Park, Ill.).

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

A "solid support", refers to any material which is insoluble, or can be made insoluble by a subsequent reaction. Thus, a solid support can be can be latex, plastic, derivatized plastic, magnetic or non-magnetic metal, glass, silicon or the like. A vast array of solid support configurations are also well known and include, but are not intended to be limited to, beads, shavings, grains, particles, plates, or tubes.

According to one embodiment, hybrids can be detected by incorporating labels in the primer and/or probe sequences to facilitate detection. Hence, first and second specific binding members attached to the primers and probes can be employed to immobilize the hybrids to, for example, microparticles and detect the presence of the hybrids on the microparticles with the assistance of a conjugate.

According to another embodiment, a combination of specific binding members and directly detectable labels can be employed to detect hybrids. For example, specific binding members can be introduced in the hybrids using primers labeled with specific binding members. A directly detectable label can be incorporated into the hybrids using a probe that has been labeled with a directly detectable label. Hence, hybrids can be immobilized to a microparticle using the specific binding member and directly detected by virtue of the label on the probe. It will be understood that other detection configurations are a matter of choice for those skilled in the art.

According to a preferred embodiment, "oligonucleotide hybridization PCR" (variably referred to herein as "OH PCR") amplification reaction as described in U.S. patent application Ser. No. 08/514,704, filed Aug. 14, 1995, that is herein incorporated by reference, is employed to detect the target sequence. Briefly, the reagents employed in the preferred method comprise at least one amplification primer and at least one internal hybridization probe, as well amplification reagents for performing an amplification reaction. The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

According to the above preferred embodiment the probe initially is part of the reaction mixture, it is preferable to select primers, probes and amplification conditions such that the probe sequence has a lower melt temperature than the primer sequences so that upon placing the reaction mixture under amplification conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

The following examples are provided to further illustrate the present invention and not intended to limit the invention.

EXAMPLES

The following examples demonstrate detection of a single nucleotide polymorphism in the beta-2 adrenergic receptor gene using the DNA oligomer primers and probes herein provided. These DNA primers and probes are identified as SEQUENCE ID NO. 2, SEQUENCE ID NO. 3, SEQUENCE ID NO. 4 and SEQUENCE ID NO. 5. A portion of a representative sequence from the beta-2 adrenergic receptor gene is designated herein as SEQUENCE ID NO. 1.

In the following examples, SEQ ID NO. 2 and SEQ ID NO. 3 are used as amplification primers specific for a portion of both the wild type and mutant beta-2 adrenergic receptor gene. SEQ ID NO. 4 is an internal hybridization probe that detects the wild type allele of the beta-2 adrenergic receptor gene amplification product. SEQ ID NO. 5 is an internal hybridization probe that detects the mutant allele of the beta-2 adrenergic receptor gene amplification product.

Example 1

Preparation of Beta-2 Adrenergic Receptor Gene Primers and Probes

A. beta-2 Adrenergic Receptor Primers Primers were designed to bind and allow amplification of the target sequence containing both wild type and mutant alleles of the beta-2 adrenergic receptor gene by oligonucleotide hybridization PCR. These primers were SEQ ID NO. 2 and SEQ ID NO. 3. Primer sequences were synthesized using standard oligonucleotide synthesis methodology. Additionally, SEQ ID NO. 3 was haptenated with carbazole at the 5' end using standard cyanoethyl phosphoramidite coupling chemistry as described in U.S. Pat. No. 5,424,414 incorporated herein by reference.

B. Wild Type and Mutant beta-2 Adrenergic Receptor Probes Probes were designed to hybridize with the amplified target sequence of either the wild type or mutant allele in the beta-2 adrenergic receptor gene by oligonucleotide hybridization. These probes were SEQ ID NO. 4 for the wild type allele, and SEQ ID NO. 5 for the mutant allele. Probe sequences were synthesized using standard oligonucleotide synthesis methodology. SEQ ID NO. 4 was haptenated with an adamantane at the 5' end followed by 10 thymidines, and blocked with phosphate at the 3' end. SEQ ID NO. 5 was haptenated with a dansyl at the 5' end followed by 10 thymidines, and blocked with phosphate at the 3' end. All syntheses used standard cyanoethyl phosphoramidite coupling chemistry as described in U.S. Pat. No. 5,464,746 (herein incorporated by reference).

Example 2

Detection of Beta-2 Adrenergic Receptor Polymorphism

A. General Procedure DNA was extracted from whole blood using either the QIAamp® Blood Mini Kit (for samples less than or equal to 200 μl) or the QIAamp® Blood Maxi Kit (for sample volumes from 200 μl to 10 ml) (both kits from Qiagen, Valencia, Calif.) per the manufacturer's directions. The genotype of all samples was verified by sequencing. This allowed samples to be identified as either homozygous wild type, homozygous mutant or heterozygous at the beta-2 adrenergic receptor gene allele being tested for herein. In some cases, the purified DNA was quantitated by spectrophotometry.

DNA from the above samples was PCR amplified and detected using SEQ ID NO. 2 and SEQ ID NO. 3 primers with SEQ ID NO. 4 (wild type) and SEQ ID NO. 5 (mutant) probes as prepared in Example 1.

PCR was performed in 1×OH buffer containing 50 mM N,N,-bis[2-Hydroxyethyl] glycine (Bicine), pH 8.1, 150 mM potassium acetate, 0.1 mM ethylene diaminetetra-acetic acid, 0.02% sodium azide, 0.001% bovine serum albumin and 8% (w/v) glycerol. Recombinant *Thermus thermophilus* DNA polymerase was used at a concentration of 5 units/reaction, with dNTPs (dATP, dGTP, dTTP and dCTP) present at a final concentration of 150 μM each. SEQ ID NO. 2 and SEQ ID NO. 3 primers and the SEQ ID NO. 4 wild type probe were used at a concentration of 110 nM each, and the SEQ ID NO. 5 mutant probe was used at a concentration of 50 nM. A final concentration of 3.25 mM manganese chloride was also present in the reaction mixture. The total reaction volume was 0.2 ml, with a sample volume of 20 μl.

Reaction mixtures were amplified in an LCx® Thermal Cycler. Reaction mixtures were first incubated at 97° C. for 2 minutes, followed by 45 cycles of PCR amplification at 94° C. for 40 seconds, 55° C. for 40 seconds then 72° C. for 40 seconds. After the reaction mixtures were thermal cycled, the mixtures were maintained at 97° C. for 5 minutes and probe oligo hybridization was accomplished by rapidly lowering the temperature to 12° C. Samples were held at 12° C. for a minimum of 10 minutes, and thereafter until reaction products were analyzed and detected.

Reaction products were detected on the Abbott LCx® system (available from Abbott Laboratories, Abbott Park, Ill.). A suspension of anti-carbazole coated microparticles, an anti-adamantane antibody/alkaline phosphatase conjugate and an anti-dansyl antibody/β-galactosidase conjugate (available from Abbott Laboratories, Abbott Park, Ill.) were used in conjunction with the LCx® to capture and detect the reaction products. The enzyme substrates used were 4-methyl-umbelliferyl phosphate (MUP) and 7-β-D-galactopyranosyloxy coumarin-4-acetic acid-(2-hydroxyethyl) amide (AUG) with the rate of conversion of substrate to product measured and reported as counts/second/second (c/s/s).

B. Target DNA Titration DNA from each of the 3 genotypes (homozygous wild type, heterozygous and homozygous mutant), verified by sequencing, was isolated, quantitated and tested by the procedure above using varying amounts of DNA, from 25 ng per reaction to 500 ng per reaction, in the sample.

Data from this experiment is presented in TABLE 1 and shows that the wild type probe detected both the homozygous wild type and heterozygous beta-2 adrenergic receptor genotypes but did not detect the homozygous mutant beta-2 adrenergic receptor genotype as positive. The mutant probe detected both homozygous mutant and heterozygous beta-2 adrenergic receptor genotypes but did not detect the homozygous wild type beta-2 adrenergic receptor genotype as positive. As expected, both probes detected the heterozygous samples since they contain one wild type and one mutant allele. Additionally, the LCx reaction rate of the heterozygous samples was approximately half that of the homozygous samples, since the probe would have only one allele to react with rather than the 2 alleles present in the appropriate homozygous sample. Thus, all probes showed excellent specificity. All positive samples were detectable down to at least 25 ng of DNA per reaction.

TABLE 1

| beta-2 Adrenergic Receptor Genotype | DNA (ng) | | | | | | |
|---|---|---|---|---|---|---|---|
|  | 25 | 50 | 100 | 200 | 300 | 400 | 500 |
| LCx ® rate (c/s/s) of Wild Type Probe | | | | | | | |
| Homozygous wild type | 747.3 | 794.8 | 819.2 | 931.4 | 924.8 | 882.0 | 831.5 |
| Heterozygous | 438.4 | 502.9 | 530.8 | 497.8 | 558.8 | 567.3 | 529.0 |
| Homozygous mutant | 52.5 | 51.9 | 56.5 | 55.9 | 62.8 | 82.4 | 66.7 |
| LCx ® rate (c/s/s) of Mutant Probe | | | | | | | |
| Homozygous wild type | 46.9 | 48.7 | 87.4 | 59.6 | 53.2 | 54.9 | 54.2 |
| Heterozygous | 566.2 | 662.9 | 668.1 | 679.1 | 746.3 | 768.6 | 737.3 |
| Homozygous mutant | 964.8 | 1068.8 | 1105.9 | 1128.5 | 1209.9 | 1195.7 | 1206.4 |

C. Genotype Determination of Unknown Samples The procedure described in A. above was used to determine the beta-2 adrenergic receptor genotype of 20 samples. This result was then compared to that determined by sequencing.

As can be seen in TABLE 2, samples clearly reacted with only the wild type probe (homozygous wild type), only the mutant probe (homozygous mutant) or both probes (heterozygous). These results were verified by sequencing. Thus this method, using these primers and probes in the LCx format, is as accurate for determining the genotype at the beta-2 adrenergic receptor as sequencing, while being easier to perform.

TABLE 2

| Sample No. | Wild Type Probe LCx ® rate | Mutant Probe LCx ® rate | Genotype |
|---|---|---|---|
| 1 | 68.6 | 1115.5 | Homozygous mutant |
| 2 | 74.9 | 1118.1 | Homozygous mutant |
| 3 | 67.6 | 1109.2 | Homozygous mutant |
| 4 | 65.4 | 1118.0 | Homozygous mutant |
| 5 | 70.4 | 1173.7 | Homozygous mutant |
| 6 | 68.5 | 1061.3 | Homozygous mutant |
| 7 | 69.7 | 1061.6 | Homozygous mutant |
| 8 | 70.3 | 1083.7 | Homozygous mutant |
| 9 | 70.8 | 1194.2 | Homozygous mutant |
| 10 | 75.7 | 1163.6 | Homozygous mutant |
| 11 | 77.4 | 1166.2 | Homozygous mutant |
| 12 | 597.8 | 692.2 | Heterozygous |
| 13 | 564.6 | 675.0 | Heterozygous |
| 14 | 578.6 | 630.6 | Heterozygous |
| 15 | 637.5 | 677.1 | Heterozygous |
| 16 | 595.0 | 685.6 | Heterozygous |
| 17 | 594.1 | 663.1 | Heterozygous |
| 18 | 963.2 | 52.6 | Homozygous wild type |
| 19 | 878.6 | 51.6 | Homozygous wild type |
| 20 | 897.6 | 50.6 | Homozygous wild type |

While the invention has been described in detail and with reference to specific embodiments, it will be apparent to one skilled in the art that various changes and modifications may be made to such embodiments without departing from the spirit and scope of the invention.

What is claimed is:

1. A combination of nucleic acids comprising a first nucleic acid consisting of the nucleotide sequence SEQ ID NO. 2 and optionally one or more labels, and a second nucleic acid consisting of the nucleotide sequence SEQ ID NO. 3 and optionally one or more labels.

2. A combination of nucleic acids for detecting a target sequence comprising a first nucleic acid consisting of the nucleotide sequence SEQ ID NO. 2 and optionally one or more labels, a second nucleic acid consisting of the nucleotide sequence SEQ ID NO. 3 and optionally one or more labels, and a third nucleic acid consisting of a nucleotide sequence selected from the group consisting of SEQ ID NO. 4 and SEQ ID NO. 5, and optionally one or more labels.

3. A method of amplifying a β2 adrenergic receptor target sequence comprising the steps of:
    (a) forming a reaction mixture comprising nucleic acid amplification reagents, the combination of nucleic acids of claim 1, and a test sample suspected of containing the target sequence; and
    (b) subjecting the mixture to amplification conditions to generate at least one copy of the target sequence.

4. A method for detecting a target sequence in a test sample comprising the steps of:
    (a) forming a reaction mixture comprising nucleic acid amplification reagents, the combination of nucleic acids of claim 1, and a test sample suspected of containing the target sequence;
    (b) subjecting the mixture to amplification conditions to generate an amplification product;
    (c) hybridizing a probe consisting of a nucleotide sequence selected from the group consisting of SEQ ID NO. 4 and SEQ ID NO. 5, and optionally one or more labels, to the amplification product to form a hybrid; and
    (d) detecting the hybrid as an indication of the presence of the target sequence in the test sample.

5. A kit for amplifying a β2 adrenergic receptor target sequence comprising:
    (a) a first nucleic acid consisting of the nucleotide sequence SEQ ID NO. 2 and optionally one or more labels, and a second nucleic acid consisting of the nucleotide sequence SEQ ID NO. 3 and optionally one or more labels; and
    (b) amplification reagents.

6. The combination of nucleic acids of claim 1, wherein one or more of the nucleic acids includes said one or more labels.

7. The combination of nucleic acids of claim 2, wherein one or more of the nucleic acids includes said one or more labels.

8. The method of claim 4, wherein the probe includes said one or more labels.

9. The kit of claim 5, wherein the first nucleic acid includes said one or more labels.

10. The kit of claim 5, wherein the second nucleic acid includes said one more labels.

* * * * *